US005467764A

United States Patent [19]

Gamow

[11] Patent Number: 5,467,764

[45] Date of Patent: Nov. 21, 1995

[54] HYPOBARIC SLEEPING CHAMBER

[75] Inventor: Rustem I. Gamow, Boulder, Colo.

[73] Assignee: Hyperbaric Mountain Technologies, Inc., Boulder, Colo.

[21] Appl. No.: 61,275

[22] Filed: May 13, 1993

Related U.S. Application Data

[63] Continuation of Ser. No. 837,760, Feb. 19, 1992, abandoned.

[51] Int. Cl.[6] .............................. A62B 18/08; A62B 7/00; A61M 15/00

[52] U.S. Cl. .............................. 128/202.12; 128/200.24

[58] Field of Search .............................. 128/200.24, 202.12, 128/205.26; 600/21, 22; 482/13, 148

[56] References Cited

U.S. PATENT DOCUMENTS

| | | | |
|---|---|---|---|
| 1,294,188 | 2/1919 | Stelzner et al. . | |
| 2,401,230 | 5/1946 | Colley et al. . | |
| 2,824,557 | 2/1958 | Mejean et al. | 128/202.11 |
| 3,387,412 | 6/1968 | Kwake | 128/205.26 |
| 3,602,221 | 8/1971 | Bleicken | 128/205.26 |
| 3,729,002 | 4/1973 | Miller et al. . | |
| 3,801,093 | 4/1974 | Jones, III | 272/3 |
| 4,106,504 | 8/1978 | York et al. . | |
| 4,189,725 | 2/1980 | Rowland et al. . | |
| 4,274,405 | 6/1981 | Schmidt et al. | 128/205.26 |
| 4,462,246 | 7/1984 | Advani et al. . | |
| 4,467,798 | 8/1984 | Saxon et al. | 128/202.12 |
| 4,621,621 | 11/1986 | Marsalis et al. . | |
| 4,633,859 | 1/1987 | Reneau | 128/205.26 |
| 4,914,424 | 4/1990 | Hirao et al. . | |
| 4,974,829 | 12/1990 | Gamow et al. . | |
| 5,063,924 | 11/1991 | Galvan et al. . | |
| 5,101,819 | 4/1992 | Lane | 128/204.18 |

FOREIGN PATENT DOCUMENTS

| | | | |
|---|---|---|---|
| 7900526 | 8/1979 | WIPO | 128/202.26 |

OTHER PUBLICATIONS

*Pneumatic Structures*, Minke & Eggers, Crosby Lockwood Staples, London. ©1976.

Johnson, D. L., "Hearing Hazards Associated with Infrasound", in New Perspectives on Noise–Induced Hearing Loss, Hamernik, R. P., Henderson, D. and Salvi, R. (eds.) 1982, 407–421.

Slarve, R. N. and Johnson, D. L., "Human Whole–Body Exposure to Infrasound", Aviation, Space, and Environmental Medicine (Apr. 1975), 428–431.

Johnson, D. L., "Effects of Infrasound on Respiration", Preprints of 1973 Annual Scientific Meeting of Aerospace Medical Assn (May 1973) 37–38.

Levine, B. D. et al. (Apr. 1991) Medicine and Science in Sports and Exercise 23(4), Suppl. 145.

May, C. (Nov. 1990) "The Town That Can't Sit Still," New York Times, p. 58.

Richalet, J. P. Abstract 90, The Seventh International Hypoxia Symposium.

Escoffier, E. (1990) "Everest Attempt and Acclimatization Experiment" The American Alpine Journal, pp. 303–304.

Endo, Y. (1989) "High Mountain Research Center, Nagoya, Japan," The American Alpine Journal, p. 266.

*Primary Examiner*—Kimberly L. Asher

*Attorney, Agent, or Firm*—Greenlee and Winner

[57] ABSTRACT

A portable hypobaric sleeping chamber for acclimatization to high altitude or athletic conditioning is provided, capable of maintaining internal pressures about 0.1 to about 10 psi below ambient.

6 Claims, 2 Drawing Sheets

HYPOBARIC SLEEPING CHAMBER

This is a continuation of application Ser. No. 07/837,760, filed on Feb. 19, 1992, now abandoned.

FIELD OF THE INVENTION

This invention lies in the field of hypobaric body chambers.

BACKGROUND OF THE INVENTION

For many years there has been a raging battle concerning the wisdom of high altitude training for the low altitude athlete. Advocates of high altitude training cited the numerous studies that all show that the number of red blood cells increased and the aerobic capacity increased after some extended stay at altitude, i.e., after acclimatization. Opponents to altitude training for the sea level athletes, while acknowledging the increase in the hemoglobin in these subjects, cited well-documented evidence that since the performance of the athlete was so poor at altitude, a maximum training regime was never possible to initiate. Thus, maximum training could never occur. One clear solution that would answer both objections would simply have the athlete live at altitude but train at sea level. In this way he or she would obtain the maximum benefit from both the high altitude and low altitude physiology. Since de-acclimatization takes several weeks, there is virtually no effect if the athlete descends quickly to sea level for training and then reascends for the rest of his or her nontraining time. This descent could be done either by physically transporting the person to or near sea level or accomplishing the same effect via a hyperbaric chamber.

Recently there was a report from Salt Lake City (Levine, B. D. et al. (Apr 1991) Medicine and Science in Sports and Exercise 23(4), Suppl. 145; and Levine, B. D. and Houston, C., "Benefits of training at high altitude: myth or reality," The Seventh International Hypoxia Symposium) clearly demonstrating that athletes living at Snowbird, Utah (8,000 ft.), but training at Salt Lake City, Utah (4,500 ft.), were significantly more fit than the control group that both lived and trained at Salt Lake City.

Presently the Olympic Training Center (OTC) in Colorado Springs is repeating this study and taking it further (May, C. (November 1991), "The Town That Can't Sit Still," *New York Times Magazine*, p. 58). The OTC is comparing and contrasting four situations: 1. Live high and train high; 2. Live low and train low; 3. Live low and train high; and 4. Live high and train low. These studies all deal with determining the fitness level of athletes such as runners and bicyclists, but there have also been several reports that high altitude climbers that spent time in a hypobaric chamber (altitude chamber) previous to climbing a mountain at altitude were better acclimatized when starting the climb because of the time spent in the hypobaric chamber (Richalet, J. P., "Effects of Acute and Chronic Hypoxia in Human Erthropoeitin Control at Rest and Exercise," Abstract 90, The Seventh International Hypoxia Symposium; Escoffier, E. (1990), "Everest Attempt and Acclimatization Experiment," *The American Alpine Journal*, pp. 303–304; and Endo, Y. (1989), "High Mountain Research Center, Nagoya, Japan," *The American Alpine Journal*, p. 266). These two lines of evidence both show that time spent at altitude results in an increase in the number of red blood cells which is reflected in the acclimatization in the mountain climbers as it also is in athletes.

Previously-known hypobaric chambers have been large, heavy structures with walls made of structurally rigid materials such as concrete or metal which can simulate altitudes of 50,000 to several hundred-thousand feet and are used for such purposes as pilot training.

Portable hyperbaric chambers are known. For example, U.S. Pat. No. 4,974,829 to Gamow et al. discloses a spherical-shaped hyperbaric chamber useful for physical conditioning for athletes, and a cylindrically-shaped hyperbaric mountain bag in which mountain climbers suffering from altitude sickness can be placed in a higher pressure equivalent to descent to a lower altitude for alleviation of their symptoms.

U.S. Pat. No. 5,063,924 to Galvan et al. discloses a portable enclosed chamber for providing a controlled atmosphere which may be pressurized to aid individuals in breathing in toxic atmospheres.

U.S. Pat. No. 4,106,504 to York discloses a portable recompression chamber capable of being pressurized to a desired ocean depth pressure U.S. Pat. No. 3,729,002 to Miller discloses a portable, collapsible recompression chamber for achieving ocean depth pressures.

U.S. Pat. No. 2,401,230 to Colley discloses a portable hyperbaric chamber capable of pressurization for use during air flight at high altitudes.

U.S. Pat. No. 1,294,188 to Stelzner discloses a portable, collapsible decompression chamber which can be pressurized to ocean depth pressures.

U.S. Pat. No. 4,621,621 to Marsalis discloses a portable hypobaric device which is a respirator breathing jacket. The jacket assembly has a screen-like grid curved to fit over the torso of the user in spaced apart position from the torso, with an airtight poncho-like jacket positioned over the grid. A vacuum pump and valve assembly allows air to be alternately exhausted from and communicated into the jacket to cause the user to inhale and exhale.

Oxygen monitoring devices are also known to the art, e.g., as described in U.S. Pat. Nos. 4,914,424 to Hirao et al,; 4,462,246 to Advani et al.; and 4,189,725 to Rowland et al.

None of the foregoing patents disclose a lightweight, portable hypobaric chamber designed for only one or two reclining persons.

SUMMARY OF THE INVENTION

Figure 1:
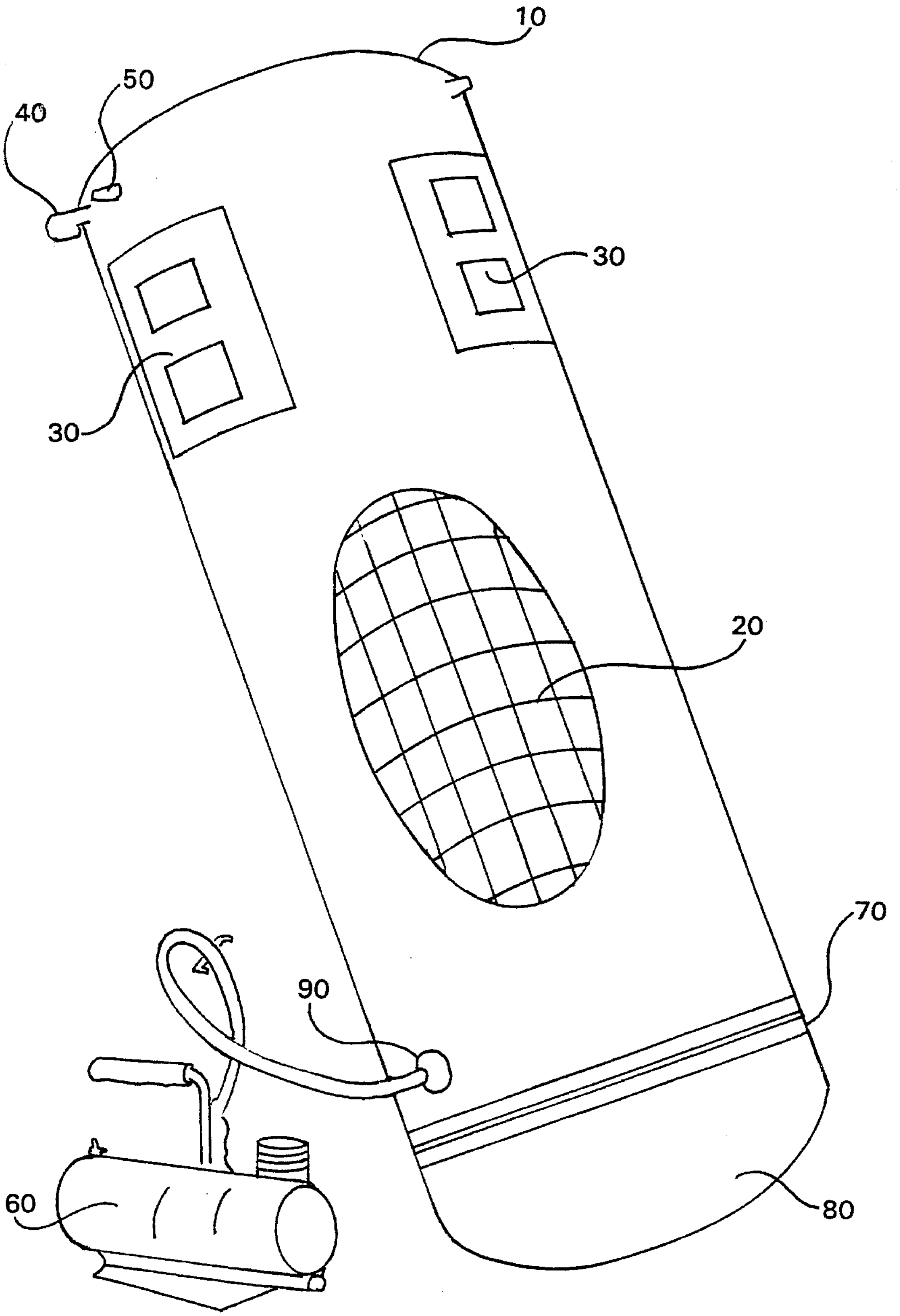
FIG. 1 depicts a preferred embodiment of the hypobaric chamber of this invention and attached vacuum pump with a section of the outer material of the chamber shown as though cut away to display the inner support frame.

A portable hypobaric chamber in cylindrical or spherical form, sized to accommodate no more than two reclining humans is provided, which is capable of maintaining at least about 0.1 psi below ambient air pressures comprising:

a. a rigid air-impermeable, preferably nonelastomeric flexible material;

b. substantially airtight ingress and egress means through said air-impermeable material of a size sufficient to allow a human to pass therethrough;

c. a vacuum release valve in said air-impermeable material;

d. a vacuum maintenance orifice in said air-impermeable material through which air may be removed from said chamber.

The chamber may also comprise an internal support frame where the air-impermeable material is not self-supporting.

The portable hypobaric chamber of this invention may be used for both the acclimatization of the high altitude climber and as a method to increase aerobic capacity for the athlete. This chamber allows both the low altitude athlete and the high altitude climber to gain the advantage of altitude acclimatization while remaining at or near sea level. The chamber should be large enough and comfortable enough that a person could sleep in the chamber and thus spend perhaps as much as eight hours a day in the chamber. The chamber of this invention weighs less than 2,000 pounds, preferably less than 100 pounds, and more preferably less than 50 pounds, and can simulate altitudes up to three miles (approximately 16,000 ft), i.e., about 0.1 to about 10 psi below ambient air pressure at sea level. In a preferred embodiment no carbon dioxide scrubbers are needed. The device simply rapidly exchanges the ambient air with the air in the chamber. This is because as the pressure is decreased in the chamber the vacuum pressure relief valves open, pulling in fresh air full of oxygen and simultaneously eliminating the $CO_2$ buildup in the bag.

The portable hypobaric chamber has a volume large enough so one or two people may sit or lie comfortably for four to eight hours. A cylinder approximately six feet long and 16 inches in diameter is a preferred minimum size for use by an adult human. A size that appears to maximize the comfort volume with minimum bulk to accommodate one or two users is approximately seven feet long and approximately 31 inches in diameter, i.e., about 37 cubic feet.

The outer material of the chamber is any air-impermeable material, preferably a fabric such as a coated nylon or mylar. Preferably the material is essentially nonelastomeric and flexible.

The chamber is equipped with one or more vacuum release valves which open allowing ambient air from the outside to enter the chamber when the desired gauge pressure is obtained. The vacuum release valves are adjusted to allow a gauge pressure from 0.1 psi gauge to 10.00 psi gauge with the lower pressure always being in the chamber.

An internal frame of a rigid or semi-rigid material, preferably steel or synthetic mesh material, e.g., braided carbon composite may be placed in the chamber. The frame may include solid (nonmesh) portions such as metal or fiberglass end caps or plates which can be equipped with means for ingress and egress. Preferably the frame is slightly larger than the volume of the outer material so that the outer material is under tension when stretched over the frame. The outer material then helps maintain the cylindrical or spherical shape of the frame even under hypobaric pressure. The outer material serves to keep the ambient pressure from entering the chamber and the internal frame keeps the chamber from collapsing. The frame may also be slightly smaller than the outer material if prestressing of the outer material is not required for maintaining the shape of the chamber.

The chamber has one to several optional windows. When the outer material is not transparent, it is preferred that it be provided with an opening for a window wherein said window is comprised of a transparent or translucent material which may be sewn or heat-sealed in said opening. The chamber also has airtight means for ingress and egress, such as a door, preferably self-sealing, and/or a zipper when a fabric outer material is used. The zipper placement, for optimal comfort, is at the end of the chamber placed circumferentially around the chamber for minimum stress. When the frame includes solid metal parts equipped with means for ingress and egress, such means are preferably substantially airtight, e.g., having rubber seals such as those used on refrigeration doors. A mylar outer material can have ingress and egress means comprising openings closed by flaps or folding, and sealed with tape.

A vacuum pump is attached to a one-way valve for removing air from the chamber to achieve the desired pressure. The chamber is preferably also equipped with a pressure gauge or an altimeter and a commercial oximeter having an $O_2$ alarm feature.

DETAILED DESCRIPTION OF THE PREFERRED EMBODIMENTS

A hypobaric chamber is provided for simulating altitudes higher than those at which the chamber is being used. The chamber is portable, preferably cylindrical in shape and preferably no larger than required to accommodate two reclining adult humans. The preferred volume is about 37 cubic feet, i.e., about seven feet long and about 31 inches in diameter. A preferred minimum size for use by an adult human would be about six feet long and about 16 inches in diameter. Chambers designed for use by children, animals or other purposes may be smaller as required. The chamber may be larger, but to maintain a preferred weight of 100 pounds or less, in accordance with the discussion hereinafter, the size cannot be radically increased because the strength required for the frame and outer material goes up rapidly in proportion to the square of the interior radius.

The chamber is capable of simulating altitudes up to about 16,000 feet, i.e., about 10 psi below ambient pressure at sea level. Pressures in the chamber can be maintained at between about 0.1 and about 10 psi below the ambient pressure at the location where the chamber is used. The vacuum pump exhausts air through an outlet in the chamber until a preset pressure level is reached within the chamber. When the preset pressure level is passed (that is when the pressure inside the chamber is lower than the preset level), a vacuum release valve allows air from outside the chamber to enter the chamber until the desired pressure is again achieved.

With the vacuum pump, which is preferably automatically powered, running continuously, a constant supply of fresh air will enter the chamber through the vacuum release valve so that there will be no need to supply the user inside the chamber with oxygen from another source or to provide other expedients for removing carbon dioxide.

The chamber comprises an internal support frame, if needed, preferably a grid made of a rigid or semi-rigid material such as metal or composite plastic. To minimize the weight and maximize the portability of the device, the grid may be less rigid than required to maintain the chamber's shape when not in use. For example, the grid may be comprised of thin, semi-rigid wires or strands which allow deformation or folding of the grid when the chamber is not pressurized. Upon achieving hypobaric pressure in the chamber, if the chamber is spherical or cylindrical in shape, the pressure of the outer atmosphere acting uniformly on the outer material covering the grid will cause the chamber to assume and maintain its shape. Thus, spherical or cylindrical shapes are preferred.

Those skilled in the art will be able, without undue experimentation, to determine optimal strength, flexibility and size of the openings in the grid depending on such factors as the strength and flexibility of the outer material, the desired internal pressure, and the size of the chamber.

The structural mechanics of thin cylindrical shells under external pressure has been well studied and is well understood. The following calculations show the relationship between a number of variables such as chamber size, and strength and elasticity of the materials used. Given the dimensions of the cylindrical chamber, one can readily calculate the safe differential pressure between the inside and the outside of the chamber, i.e., psig. The pressures involved are identical to those "felt" by a cylindrical submarine. Given the yield strength of the material ($\sigma_y$) and the modulus of elasticity (E), the following formula $$q^1 = \frac{t}{R} \quad \frac{\sigma_y}{1 + (4\sigma_y/E)\,(R/Ert)^2}$$

will yield the external collapsing pressure ($q^1$). Using a 3/16" thick (t) mild steel that has been shaped into a cylinder 7 ft long with a radius (R) of 15.5", the collapsing pressure ($q^1$) of the cylinder will be 13 psig. Using mild steel ¼" thick gives a collapsing pressure ($q^1$) of 30 psi. A chamber with the external dimensions described above with walls of mild steel 3/16" thick will have a safety factor of a little less than three when ascended to an equivalent altitude of 3,000 m (9,840 ft) from sea level. This safety factor is calculated in the following way. At an altitude of 3,000 m (9,840 ft) the barometric pressure is 10.2 psi, i.e., psig of 4.5 in respect to sea level. At a much higher altitude of 5,000 m (16,404 ft) the barometric pressure is 7.8 psi, i.e., psig of 6.9 giving us a safety factor of a little less than two. We thus suggest for simulated altitude greater than 3,000 m a wall thickness of ¼" mild steel should be used. Such a chamber has a collapsing pressure ($q^1$) of 30 psig.

The calculations above describe the use of a mild steel material only without interior supports, however, it will be apparent therefrom to those skilled in the art how the various variables may be changed to provide alternative embodiments of this invention. It is important to prevent buckling of the outer material when no internal frame is used, or of the internal frame. Using modern composite material such as woven carbon fibers embedded in a resin such as epoxy and adding circumferential load supporting ribs to the cylinder allows one to use thinner and lighter materials. A variety of preferably collapsible internal frames whose stiffness is maintained by a series of interlocking units, some of which can be prestressed by the outer material as described herein, are preferably substituted for the mild steel skin. The internal frame preferably includes annular rings made of a rigid material disposed at least at the ends of the cylinder, and optionally spaced apart along the length of the cylinder.

Composite plastic wands, e.g., of the type used as tent supports, may also be used to construct an internal support, for example, by insertion through loops or channels on the inner surface of the outer material of the chamber. Another preferred material for construction of the frame is braided carbon fiber composite, available from Engineering Innovations, Littleton, Colo. This material is available in the form of hollow pipes which can be used to construct the frame.

Optional end caps such as shown in FIG. 1 made of a rigid material such as metal, plastic or fiberglass may also comprise part of the internal support frame for the chamber. In one embodiment the end caps are designed to fit together to form a carrying case for the chamber when collapsed.

Figure 2:
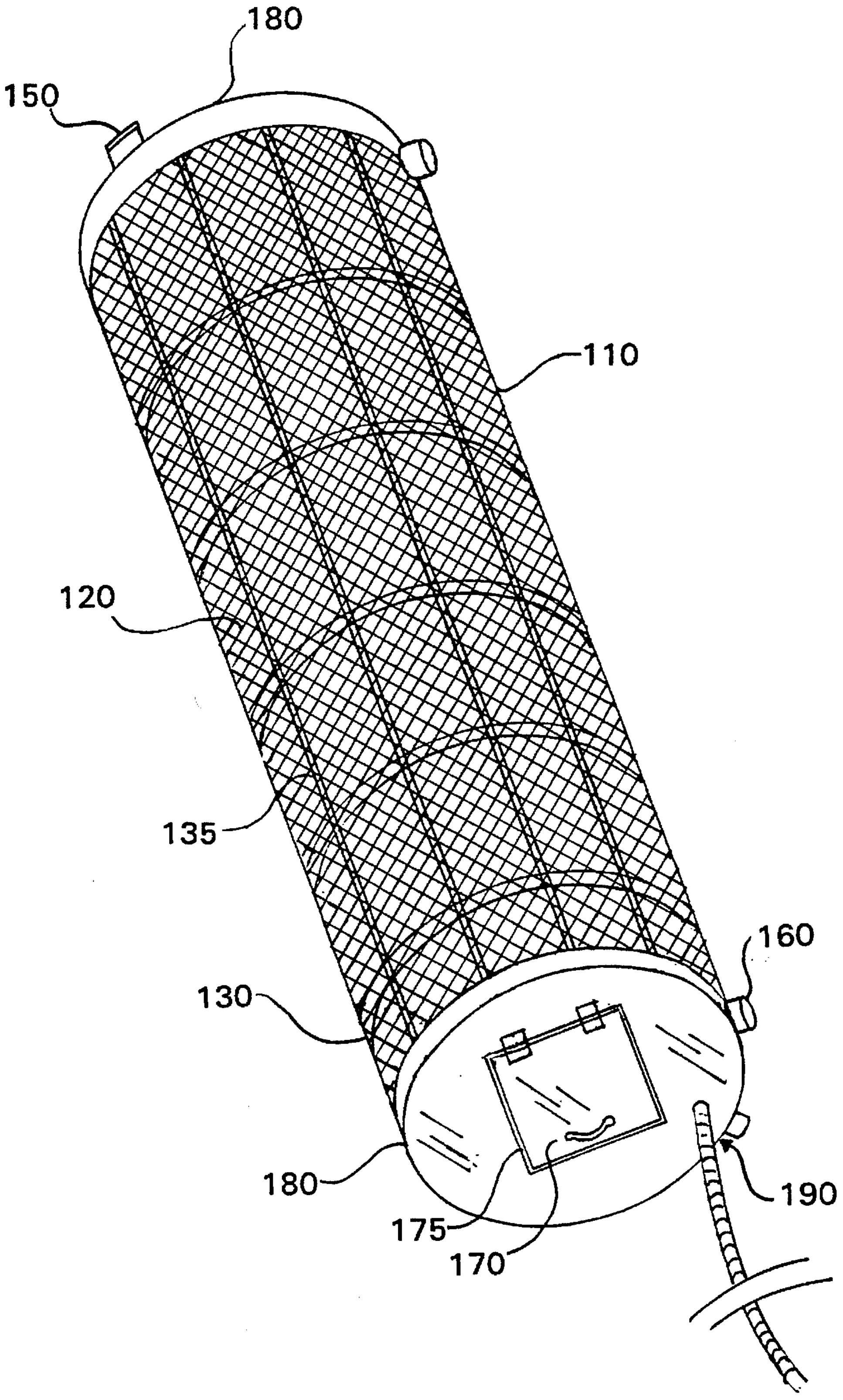
FIG. 2 depicts a preferred embodiment of the hypobaric chamber of this invention having a ribbed internal frame covered with Mylar, and steel end plates, one of which is equipped with a self-sealing door.

The frame may also include rigid end plates which can be shaped to conform to the overall cylindrical or spherical shape of the chamber or can be flat, circular plates as shown in FIG. 2. These plates may include ingress and egress means, such as a door, preferably made essentially airtight by means known to the art such as rubber seals. When the cylinder is composed of solid sheets of material without windows, it is preferred that the end plates be of transparent material.

The chamber also comprises an outer, air-impermeable material disposed about said internal frame. This outer material is preferably a flexible material such as fabric treated to be air-impermeable or mylar. The outer material may be transparent. If it is not transparent it is preferred that the outer material be equipped with one or more windows made of a transparent material to allow the occupant of the chamber to look out and be viewed by others outside the chamber monitoring its use.

The outer material should be essentially nonelastomeric so that it is capable of maintaining hypobaric pressures within the chamber without substantially stretching. However, it is desirable that enough stretch be present in the material so that when it is disposed over the internal support frame, it will be under tension. This will help the support frame to maintain its cylindrical shape. The outer material should not be so stretchy as to be pulled inside the chamber to reduce the internal volume thereof to any significant degree.

As will be appreciated by those skilled in the art, the outer material must be strong enough not to tear when stretched over the internal support frame or when the chamber is in use.

The outer material is air-impermeable and the entire chamber is constructed using airtight seams and sealants if necessary so that the chamber is substantially airtight. Minor leakage can be tolerated because the vacuum pump is continuously or intermittently operated, and air is permitted to enter the chamber through the vacuum release valve to ensure fresh air in the chamber. Coated nylon and Mylar (Trademark of DuPont) are preferred outer materials.

In the embodiment of FIG. 2, transparent Mylar is used, preferably of a thickness of 3 mil. Other transparent materials known to the art may also be used provided they have sufficient strength to withstand the pressure difference between the interior and exterior of the chamber.

In another embodiment, the entire cylinder, except for the ends, is constructed of a solid sheet of rigid material, preferably a carbon fiber composite material in sheet form. Preferably this material comprises two sheets of composite separated by a layer of aluminum honeycomb. This material may be supported by internal ribs if required, but preferably is stiff enough, i.e., has a yield strength great enough, not to require internal supports.

The vacuum release valve can be of any construction known to the art for permitting air to enter the chamber from the outside when a predetermined pressure has been reached. A standard pressure release valve inserted into the outer material of the chamber in an orientation opposite to that used for hyperbaric devices is suitable for this use. The valve can be adjustable by the user to various pressures, or can be capable of opening only at a single pressure preset for the chamber when the chamber is constructed. The valve must be capable of opening at a difference between the inside and outside pressure of between about 0.1 and 10 psi.

It will be appreciated by those skilled in the art that because the valve responds to differences between the pressures inside and outside the chamber, when the chamber is used at altitude, the pressure release valve must be set to respond to a lower pressure difference than when the chamber is used at sea level. It is desirable that the pressure inside the bag not be less than equivalent to about 15,000 to 16,000 feet of altitude.

The hypobaric chamber of this invention also comprises substantially airtight means for ingress and egress, preferably of a size sufficient to allow an adult human to enter and exit the chamber. Preferably these means comprise substantially airtight zipper means when a fabric outer material is used, preferably disposed along an axis perpendicular to the long axis of the cylindrical chamber, and preferably positioned near one end of the chamber. A door in the frame, preferably in a rigid plate portion of the frame such as the flat, circular end plate described above, can also be used, preferably a self-sealing door similar to a refrigerator. When an outer material such as mylar is used, openings closed by flaps or folding and sealed with tape may be used.

As will be readily appreciated, the openings in the outer material must coincide with openings in the internal frame such as those discussed above.

Airtight zippers are known to the art and include zippers manufactured by Talon and YKK of rubber or steel.

As will be appreciated by those skilled in the art, other ingress/egress means may be used so long as they are substantially airtight when the chamber is in use. As discussed above, some leakage in the chamber can be tolerated so long as it does not exceed the vacuum pump's ability to maintain the desired hypobaric pressure within the chamber.

The chamber is also equipped with a vacuum maintenance orifice. The vacuum pump is connected to this opening and air exits the chamber through this opening. The vacuum maintenance orifice may be equipped with check valve means allowing hypobaric pressure to be maintained within the chamber when the vacuum pump is not operating. Such valve means are necessary when a manually-operated pump rather than a gasoline-powered, electrically-powered or other automatically-powered vacuum pump is used, or when such an automatically-powered pump is operated intermittently.

The hypobaric chamber of this invention is preferably portable, weighing 100 pounds or less, and preferably 50 pounds or less.

Preferably the chamber is constructed of flexible, foldable outer material and a lightweight, foldable or disassembleable inner support frame, e.g., a lightweight metal composite or plastic grid, or a series of wands which can be assembled to form the frame and disassembled for transportation and storage.

The chamber may include rigid end caps, and these may be equipped with handles and fasteners such that they fit together to form a carrying case for the chamber. Such a carrying case may optionally be of a size large enough to accommodate the vacuum pump as well as the chamber itself so that the entire system is self-contained.

As will be appreciated by those skilled in the art, the chamber may, if desired, be equipped with oxygen supply and carbon dioxide scrubber means.

An oximeter with an alarm is preferably also included in the chamber so as to alert the user or those monitoring use of the chamber when the oxygen content of the air in the chamber falls below optimal breathing levels. Such devices are known to the art and are commercially available. An alarm may also be provided which responds to power failures to alert the user if the electrical power to the vacuum pump goes off.

The inside of the chamber may be equipped with a mattress and bedding materials for the comfort of the user sleeping in the chamber. Optional legs may be added to keep the chamber from rolling.

The chamber of this invention may also be equipped with an inner bladder such as that described in U.S. Pat. No. 5,109,837, incorporated herein by reference. In this instance, air enters the chamber through the vacuum release valve, and is breathed in through a first one-way valve into a mask affixed to the user's face. The mask is also equipped with a second one-way valve through which air is breathed out into the inner bladder. the inner bladder is connected through an opening in the outer material of the chamber to a vacuum pump which may be a bicycle or raft pump or an automatically-powered pump. As the inner bladder is emptied, the pressure inside the chamber falls below the preset level and the vacuum release valve allows air to enter the chamber, thus supplying the user with a constant supply of fresh air. The user breathes only previously unbreathed air from the inside of the chamber and exhales used air only into the inner bladder. Use of the bladder allows operation of the pump to be decreased. When a manually operated pump is used, the number of pumps required per minute is substantially decreased.

An embodiment of the hypobaric chamber of this invention is shown in FIG. 1. The chamber is comprised of an outer material 10 which is disposed or stretched over internal frame 20. The chamber may optionally be equipped with windows 30. A pressure gauge or altimeter 40 may be attached to the chamber for determining the pressure inside the chamber. The chamber is also equipped with a vacuum release valve 50 which allows ambient air to enter the chamber when further air is removed from the chamber by vacuum pump 60 through vacuum maintenance orifice 90 after the desired hypobaric pressure inside the chamber has been reached, so as to maintain the pressure inside the chamber at a preset level. The chamber is also equipped with a zipper 70 to allow a human to enter and exit the chamber. Optionally the ends of the chamber beneath the outer material are equipped with rigid caps, which in their entirely comprise, or are equipped with, a self-sealing door 80.

The chamber is used for hypobaric athletic conditioning as a sleeping chamber. The user enters the chamber through airtight zipper 70 which may be opened and closed from both inside and outside the chamber. The vacuum release valve 50 is preset to a selected hypobaric pressure. For use at sea level, preferred pressures are between about 2 psi and about 7 psi below ambient. For use at high elevations such as 5,000 feet, preferred athletic conditioning pressures are between about 2 psi and about 3 psi below ambient. When the chamber is used for acclimatization to high altitude, pressures between about 5 psi and about 10 psi below ambient are selected.

The vacuum pump is activated. The vacuum pump is connected to the chamber through an orifice in the outer material of the chamber. If the internal frame contains a rigid member, there may be a corresponding orifice therein to allow connection to the pump. Preferably the pump is an automatically-powered pump rather than a manual pump. Air is exhausted from the chamber by the pump until the preset hypobaric pressure is achieved within the chamber. The outer material 10 of the chamber is pressed against the internal frame 20 by the outer air pressure acting against the lowered pressure within the chamber. The cylindrical shape of the chamber allows the pressure against the outer material to be uniformly distributed around the circumference of the chamber, thus preventing local deformation of the internal support frame. In use the chamber maintains a uniformly cylindrical shape.

The optional end caps 80 help maintain this shape. The optional windows 30 can be used for viewing the occupant inside the chamber or for the occupant's use in seeing out of the chamber.

Pressure gauge 40 which may be placed inside or outside the chamber allows the user or others to monitor the pressure inside the chamber and make adjustments if required.

An optional oximeter having an alarm feature warns the user or person monitoring the use of the bag if the oxygen level falls below that required for breathing at the desired pressure inside the chamber.

When not in use, in a preferred embodiment, the chamber may be collapsed and stored inside rigid caps 80 which can be equipped with handles and fastenings such that they comprise a carrying case for the chamber.

FIG. 2 shows a preferred embodiment of this invention. The chamber is covered with a transparent outer material 110, preferably Mylar (trademark of DuPont). The material needs to cover only the sides of the cylindrical chamber and not the ends.

The ends of the chamber are covered by metal (preferably steel) end caps 180, one of which is equipped with a self-sealing door 170 having a vacuum gasket 175.

The internal frame of the chamber is constructed of metal, preferably steel, ribs 130 in the form of annular rings, over which is placed wire mesh 120. Structural supports 135 in the form of horizontal rigid members may also be used.

The chamber is equipped with a vacuum release valve 150 in end cap 180. The end cap 180 on the opposite side of the chamber is equipped with an exhaust port, or vacuum maintenance orifice 190 connected by a hose to a vacuum pump (not shown).

The chamber is also equipped with support legs 160 to prevent tipping and rolling.

As will be appreciated by those skilled in the art, there are many modifications which may be made to the basic design described above all within the scope and spirit of this invention.

I claim:

1. A cylindrically-shaped hypobaric sleeping chamber with a length longer than its diameter having a size sufficient to accommodate no more than two reclining humans, having means for maintaining a selected internal pressure between 0.1 and 10 psi below the local ambient air pressure, and having means for providing fresh air to occupants of said chamber over a period of up to eight hours, said chamber further comprising:

(a) an air-impermeable outer layer formed of essentially nonelastomeric material, and an inner frame of rigid or semi-rigid material, said outer layer and inner frame when formed into said cylindrically-shaped hypobaric chamber having sufficient strength to withstand an external collapsing pressure of approximately 30 psig;

(b) a substantially airtight ingress and egress means through said air-impermeable material of a size sufficient to allow a human to pass therethrough;

(c) said means for providing fresh air comprising a vacuum pressure release valve located in said air-impermeable material responsive to a predetermined decrease in said internal pressure within said hypobaric chamber below ambient pressure for pulling fresh ambient air into said chamber;

(d) said means for maintaining said selected internal pressure comprising a vacuum maintenance orifice located within said air-impermeable material through which air is removed from said chamber; and (e) said cylindrically-shaped hypobaric sleeping chamber weighing approximately 200 pounds or less.

2. The chamber of claim 1 having at least one window.

3. The chamber of claim 1 having an oximeter with an oxygen alarm.

4. The chamber of claim 1 having a self-sealing door having a vacuum gasket.

5. The chamber of claim 1 weighing less than about 100 pounds.

6. A cylindrically-shaped hypobaric sleeping chamber with a length longer than its diameter having a size sufficient to accommodate no more than two reclining humans, having means for maintaining a selected internal pressure between 0.1 and 10 psi below the local ambient air pressure, and having means for providing fresh air to occupants of said chamber over a period of up to eight hours, said chamber further comprising:

(a) an air-impermeable outer layer formed of essentially nonelastomeric material, and an inner frame of rigid or semi-rigid material, said outer layer and inner frame when formed into said cylindrically-shaped hypobaric chamber having sufficient strength to withstand an external collapsing pressure of approximately 30 psig;

(b) a substantially airtight ingress and egress means through said air-impermeable material of a size sufficient to allow a human to pass therethrough;

(c) said means for providing fresh air comprising a vacuum pressure release valve located in said air-impermeable material responsive to a predetermined decrease in said internal pressure within said hypobaric chamber below ambient pressure for pulling fresh ambient air into said chamber;

(d) said means for maintaining said selected internal pressure comprising a vacuum maintenance orifice located within said air-impermeable material through which air is removed from said chamber; and (e) said cylindrically-shaped hypobaric sleeping chamber weighing approximately 2000 pounds or less.

* * * * *